United States Patent [19]

Goldmann

[11] Patent Number: 4,464,778
[45] Date of Patent: Aug. 7, 1984

[54] X-RAY EXAMINATION MEANS

[75] Inventor: Norbert Goldmann, Spardorf, Fed. Rep. of Germany

[73] Assignee: Siemens Aktiengesellschaft, Berlin & Munich, Fed. Rep. of Germany

[21] Appl. No.: 418,777

[22] Filed: Sep. 16, 1982

[30] Foreign Application Priority Data

Sep. 16, 1981 [DE] Fed. Rep. of Germany ....... 3136806

[51] Int. Cl.³ .......................... G21K 1/04; H05G 1/58; H05G 1/66
[52] U.S. Cl. .................................... 378/150; 378/115; 378/151
[58] Field of Search .................. 378/150, 151, 91, 115, 378/116

[56] References Cited

U.S. PATENT DOCUMENTS

| | | |
|---|---|---|
| 2,497,755 | 2/1950 | Berggren .............................. 378/150 |
| 2,942,126 | 6/1960 | Silbermann . |
| 3,733,487 | 5/1973 | Louche et al. . |
| 3,857,039 | 12/1974 | Franke et al. ........................ 378/150 |
| 3,934,140 | 1/1976 | Dutertre et al. . |
| 4,097,748 | 6/1978 | Monvoisin . |
| 4,145,616 | 3/1979 | Tanabe . |
| 4,329,590 | 5/1982 | Adelmeyer ........................... 378/91 |

FOREIGN PATENT DOCUMENTS 2002634 12/1974 Fed. Rep. of Germany .
2728998  1/1979 Fed. Rep. of Germany .
2932042  2/1981 Fed. Rep. of Germany .

Primary Examiner—Alfred E. Smith
Assistant Examiner—T. N. Grigsby
Attorney, Agent, or Firm—Hill, Van Santen, Steadman & Simpson

[57] ABSTRACT

An exemplary embodiment comprises an X-ray tube having at least two selectively engageable different focal points, a primary radiation diaphragm adjusted relative to the X-ray tube, and comprising an image layer. When changing the focal point, an adjustment of the primary radiation diaphragm occurs in prior X-ray tubes, the adjustment resulting in a displacement of the illuminated beam field on the image layer. The present disclosure provides that the diaphragm plates of the primary radiation diaphragm are synchronously displaced in the same direction and by approximately the same amount by which the focal point is displaced when switching from the one to the other focal point. An inventive X-ray examination system is particularly suited for employment in X-ray diagnostics.

10 Claims, 3 Drawing Figures

4,464,778

X-RAY EXAMINATION MEANS

BACKGROUND OF THE INVENTION

The invention relates to an X-ray examination means comprising an X-ray tube with at least two different, selectively engageable focal points, comprising a primary radiation diaphragm adjusted relative to the X-ray tube, and comprising an image receiving layer.

It is standard in X-ray technology to design rotating anode tubes in such manner that the anode disk exhibits two focal point paths inclined to different degrees relative to the disk plane. A separate cathode is then allocated to each of said focal point paths. Because the focal point produced on the focal point path which is less inclined relative to the disk plane exhibits smaller axial dimensions with respect to the radial projection direction, i.e., as viewed from the image receiving layer, it is predominantly employed for producing fine-delineating X-ray exposures given simultaneous reduction of its dimensions in the direction perpendicular thereto, this being achieved by means of a corresponding dimensioning of the cathode. However, its maximally admissible dose rate is less than that of the other focal point because of its smaller surface. A larger focal point is likewise generally produced with the cathode assigned to the more greatly inclined focal point path, so that one can also work with a higher dose rate. It is a peculiarity of such X-ray examination means that the two focal points arise at different geometrical locations and switching from the one to the other focal point leads to a maladjustment of the primary radiation diaphragm. Similar to the case of a parallax shift, the switching between focal points results in an admittedly slight but nonetheless noticeable shift of the image area on the image layer plane.

This image shift, of course, becomes all the greater the farther apart the two focal points lie and the smaller the numerical value of the fraction is which derives from the ratio of the spacings focal point/diaphragm to the spacing diaphragm/image layer.

SUMMARY OF THE INVENTION

The object of the invention is to indicate a way to reduce the image shift in the image layer plane when changing the focal point given the lowest possible outlay.

Given an X-ray examination means of the type initially cited, the diaphragm plates of the primary radiation diaphragm are inventively shifted synchronously in the same direction and by approximately the same amount by which the focal point shifts when switching from the one to the other focal point. The consequence of this is that the image shift in the image layer plane does not become greater than the shift of the focal point itself.

A further reduction of the image shift in the image layer plane when switching from the one to the other focal point can be achieved when, in a further development of the invention, the shift is kept smaller than the focal point shift caused by the change of focal point, being kept smaller, for instance, by the ratio of the spacing of the focal points from the diaphragm plates of the primary radiation diaphragm to the spacing of said diaphragm plates from the image layer. As a result of such a reduction of the regulating distance of the diaphragm plates, the image shift into the image layer plane when switching from the one to the other focal point can even be entirely prevented.

A simple, subsequently supplyable structure derives when, in a development of the invention, the entire primary radiation diaphragm is shifted relative to its mount. Given this structure, commercially available primary radiation diaphragms can also be employed.

In an expedient development of the invention, the diaphragm plate carrier can be displaced in the housing of the primary radiation diaphragm. This structure is not only more visually attractive than the aforementioned embodiment, it is also less susceptible to disruption because the adjustment elements are accommodated protected in the diaphragm housing.

Further details of the invention are explained on the basis of two exemplary embodiments illustrated in Figures on the accompanying drawing sheets; and other objects, features and advantages will be apparent from this detailed disclosure and from the appended claims.

DETAILED DESCRIPTION

Figure 1:
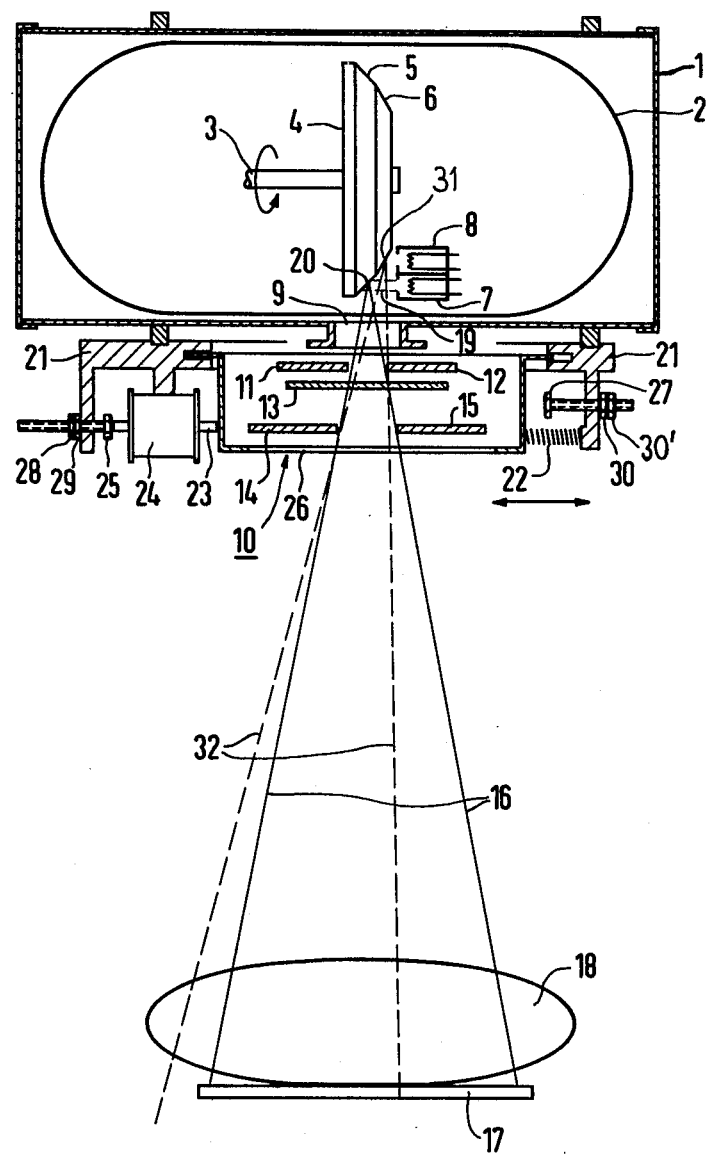
FIG. 1 shows a schematic illustration of the beam progression given an inventive X-ray examination means in which the primary radiation diaphragm is displaceable over all.

In FIG. 1, one can see an X-ray tube 2 seated in a metallic tube housing 1. Indicated in the inside of the X-ray tube 2 are an anode dish 4 rotatably mounted by means of a shaft 3 and having two focal point paths 5, 6 differently inclined relative to the dish plane, and two cathodes 7, 8 each allocated to a respective focal point path. A primary radiation diaphragm 10 is displaceably mounted at the tube housing 1 so as to be bodily adjustable parallel to the axis of the shaft 3 of the anode dish 4 and so as to be fixed at respective desired adjusted positions in front of the beam exit window 9 of the tube housing 1. Indicated at the inside of the primary radiation diaphragm 10 are the diaphragm plates 11, 12, 13, 14, 15 displaceable in various planes. An image layer 17 is disposed in the ray cone 16 stopped-down by the diaphragm plates. The image layer here optionally denotes a luminescent screen of an X-ray image intensifier or a sheet of film inserted in an X-ray film cassette. The patient 18 to be examined is indicated between the image layer 17 and the primary radiation diaphragm 10. In the illustration of FIG. 1, the cathode 7 allocated to the outer focal point path is illustrated switched-on. The electron beam 19 is illustrated with dash lines. The ray cone 16 emanating from the focus point 20 and gated onto the image layer 17 through the diaphragm plates is indicated by means of two solid lines.

As can be seen from FIG. 1, the primary radiation diaphragm 10 is displaceably mounted for adjustment parallel to the axis of shaft 3 of the anode dish 4 in a rectangular, flange-like mount 21 secured to the tube housing 1. The diaphragm housing 26 is urged by a compression spring 22 into an extreme position in which it presses the armature 23 of a solenoid 24 against a stop 25. Given excitation of the solenoid 24, the armature 23 can induce the housing 26 of the primary radiation diaphragm 10 to seat against a further stop 27 against the force of the compression spring 22. The stops 25, 27 are adjustable by means of counter-nuts 28, 29, 30, 30'.

In the fluoroscopy mode when, as illustrated in FIG. 1, the cathode 7 allocated to the more greatly inclined focal point path 5 is switched on, the solenoid 24 remains without current. In the illustration of FIG. 1, the housing 26 of the primary radiation diaphragm 10 is kept pressed toward the left in an extreme position by the compression spring 22, pressing the armature 23 of the solenoid 24 against the left detent or stop 25 in said position. The X-ray cone 16 emanating from the focal point can be adjusted relative to the image layer 17 by adjustment of the stop 25 in such manner that, given a correspondingly wide aperture of the diaphragm plates such as 11, 12, 13, 14, 15, the entire field of the image layer 17 can be exactly illuminated without edge overlap.

When the findings of the examination are then to be recorded in an X-ray exposure, then, for the purpose of examining finer details, a change can be undertaken to the cathode 8 allocated to the less inclined focal point path 6. Given an undisplaced primary radiation diaphragm 10, the ray cone 32 thus arising from focus point 31 would have the contour indicated with broken lines in FIG. 1 and would illuminate a different beam field on the image layer. In order to avoid this, the solenoid 24 is synchronously applied to voltage together with the other cathode 8. The armature 23 of the solenoid 24 presses the housing 26 of the primary radiation diaphragm 10 against the right, adjustable stop 27 in FIG. 1, the solenoid overcoming the opposing force of the compression spring 22. This stop 27 is adjusted in such manner that the new beam cone arising due to the change of the focal point is less greatly displaced than given a non-displaced primary radiation diaphragm 10. Given the displacement of the primary radiation diaphragm 10 toward the right by a specific amount in the illustration of FIG. 1, one can even achieve that the new ray cone emanating from the point of incidence of the electrons on the less inclined focal point path 6 strikes the image layer plane with the same image boundaries as the solid-line ray cone 16.

Figure 2:
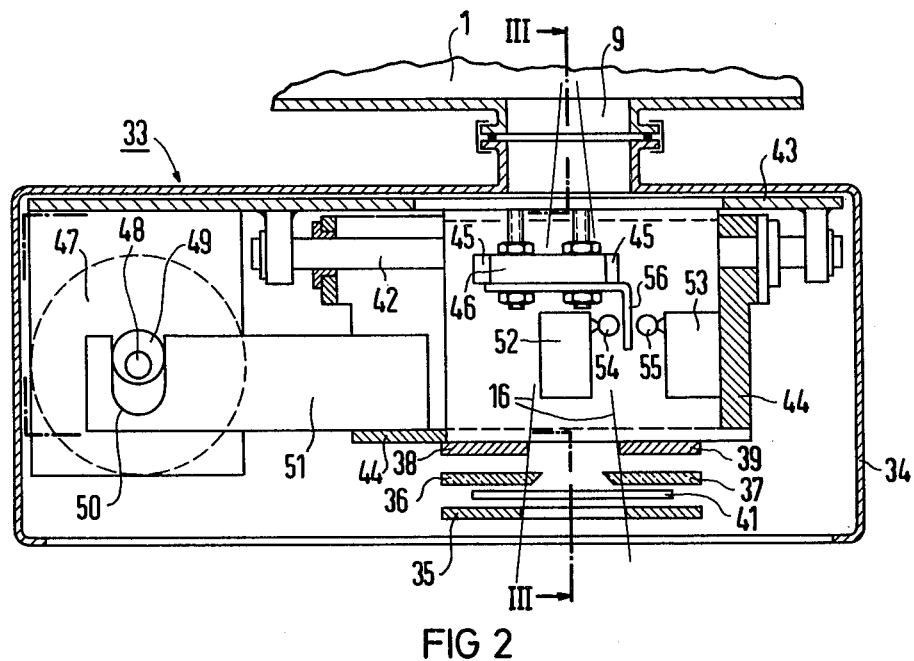
FIG. 2 shows a section through a primary radiation diaphragm in which the axis of symmetry of the gating is displaceable within the diaphragm housing.
Figure 3:
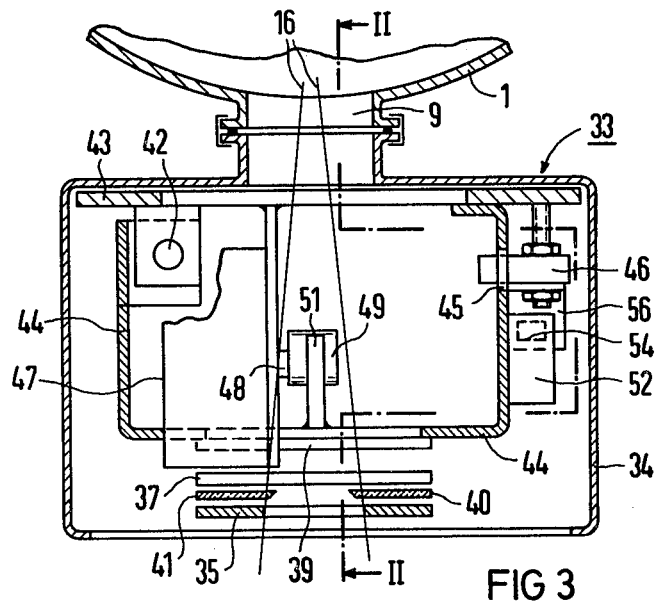
FIG. 3 shows a section taken along the line III—III of FIG. 2.

FIGS. 2 and 3 show another primary radiation diaphragm 33 given which the diaphragm housing 34 can remain immovably flanged to the X-ray tube housing 1, and the diaphragm plates 35, 36, 37, 38, 39, 40, 41 can instead be displaced in their totality in the diaphragm housing 34 of the primary radiation diaphragm 33. One can see in FIG. 2 that a guide rod 42 is mounted on a base plate 43 of the primary radiation diaphragm 33, a channel-like diaphragm carrier 44 being supported on the guide rod 42 so as to be longitudinally displaceable. As shown in FIG. 3, the diaphragm carrier 44 has a longitudinal slot aligned parallel to the guide rod 42 at its side lying opposite the guide rod 42. A low friction slider of synthetic material is height-adjustably mounted on the base plate 43 and projects into said longitudinal slot. A gear motor 47, FIG. 2, is secured to the base plate 43 next to the diaphragm carrier 44. An eccentric 49 is mounted on the motor output shaft 48. The eccentric projects into an oblong slot 50 of a dog plate 51. This is connected to the diaphragm carrier 44. The oblong slot 50 is of such width that the eccentric 49 is rotatable therein nearly without play. The setting drives for the individual diaphragm plates 35, 36, 37, 38, 39, 40, 41 are mounted on the diaphragm carrier 44 in a manner not illustrated in further detail here. Moreover, two micro-switches 52, 53 are secured to the diaphragm carrier 44, their switch rollers 54, 55 being arranged so as to be actuated by a switch angle 56 secured to the base plate 43.

The primary radiation diaphragm 33 illustrated in FIGS. 2 and 3 can be immovably secured to the flange-like designed beam exit window 9 of the X-ray tube 1. When changing the operation of the X-ray tube 2 from the one focal point to the other, the gear motor 47 is engaged over the respectively other micro-switch 52, 53. The gear motor then turns the eccentric 49 and displaces the dog plate 51 and the diaphragm carrier 44 by means of said eccentric until the micro-switch connected to voltage is switched off and the gear motor 47 stops. The diaphragm plates 35, 36, 37, 38, 39, 40, 41 together with their setting mechanisms mounted on the diaphragm carrier 44 are thus centered relative to the selected, new focal point 20, 31 in such manner that the stopped-down beam cone 16 is incident upon the same surface elements in the image layer plane as before the change of focal point. The setting of the diaphragm plates to a specific film or image format remains unaffected thereby. By means of displacing the micro-switches 52, 53 relative to the diaphragm carrier 44, the stopping points of the gear motor 47 can also be placed in such manner that the mutual spacing of the points of reversal is smaller than the maximum stroke of the eccentric.

It will be apparent that many modifications and variations may be made without departing from the scope of the teachings and concepts of the present invention.

I claim as my invention:

1. X-ray examination means comprising an X-ray tube with at least two different, selectively engageable focal points (20, 31), comprising a primary radiation diaphragm having diaphragm plates for defining an X-ray beam produced by the X-ray tube, and comprising an image layer, characterized in shifting means for synchronously shifting the diaphragm plates (11, 12, 13, 14, 15, 35, 36, 37, 38, 39, 40, 41) of the primary radiation diaphragm (10, 33) in the same direction and by approximately the same amount by which the focal point is displaced when switching from the one to the other focal point.

2. X-ray examination means according to claim 1, characterized in that the shifting of the diaphragm plates by said shifting means is kept smaller than the focal point displacement effected by the change of focal point, being kept smaller approximately by the ratio of the spacing of the focal point from the diaphragm plates (11 through 15, 35 through 41) of the primary radiation diaphragm (10, 33) relative to the spacing of said diaphragm plates from the image layer (17).

3. X-ray examination means according to claim 1, with a mount (21) for the primary radiation diaphragm secured with the X-ray tube, characterized in that the shifting means shifts the entire primary radiation diaphragm (10) relative to said mount (21).

4. X-ray examination means according to claim 1, with a housing (34) for the primary radiation diaphragm (33) having a diaphragm plate carrier (44) carrying the diaphragm plates, characterized in that the diaphragm plate carrier (44) is displaced in the housing (34) of the primary radiation diaphragm (33) by said shifting means.

5. X-ray examination means according to claim 1 characterized in that said shifting means has stops for limiting the shifting of said diaphragm plates.

6. X-ray examination means according to claim 1, characterized in that said shifting means comprises a solenoid for shifting said diaphragm plates.

7. X-ray examination means according to claim 1, characterized in that the shifting means comprises an eccentric (49) which is rotatable to effect shifting of the diaphragm plates.

8. X-ray examination means according to claim 7, characterized in that the eccentric (49) is electromotively turned.

9. X-ray examination means according to claim 4, with said shifting means comprising motor drive means mounted in said housing and coupled with said diaphragm plate carrier for positively driving the diaphragm plates as a unit between respective positions corresponding to activation of respective focal points.

10. X-ray examination means according to claim 1, with adjustable stop means having a position of adjustment defining end positions of the diaphragm plates such that the defined X-ray beam covers substantially the same area of the image layer with each of the respective focal points active.

* * * * *